United States Patent [19]

Schürle et al.

[11] Patent Number: 4,505,683

[45] Date of Patent: Mar. 19, 1985

[54] DEVICE FOR RAPID DEMONSTRATION OF THE ACTION OF PHOTOTROPIC OBJECTS

[75] Inventors: Hermann Schürle, Aalen; Wolfgang Grimm, Heidenheim; Hubert Bammert, Aalen, all of Fed. Rep. of Germany

[73] Assignee: Carl-Zeiss-Stiftung, Heidenheim, Fed. Rep. of Germany

[21] Appl. No.: 491,893

[22] Filed: May 5, 1983

[30] Foreign Application Priority Data

May 13, 1982 [EP] European Pat. Off. ........ 82104181.1

[51] Int. Cl.³ ............................................. G09B 25/00
[52] U.S. Cl. .................................................... 434/365
[58] Field of Search ....................... 434/365, 303, 366; 351/44

[56] References Cited

U.S. PATENT DOCUMENTS 2,565,079 8/1951 Kern ..................................... 434/365
3,269,267 8/1966 Collins ............................. 351/44 X Primary Examiner—Harland S. Skogquist
Attorney, Agent, or Firm—Stonebraker, Shepard & Stephens

[57] ABSTRACT

A device for rapidly demonstrating the darkening action of phototropic objects, particularly eyeglasses. The device has a housing or casing provided in its lower part (6) with a hollow space (7) which is placed over the objects to be demonstrated (8, 9) while such objects lie on any suitable horizontal supporting surface such as a table or desk. These objects are uniformly illuminated by a flash tube emitting light in the UV-A range and in the visible range. Upon each actuation of the circuit controlling the flash tube a plurality of flashes which succeed each other at a predetermined time interval is automatically given off.

6 Claims, 3 Drawing Figures

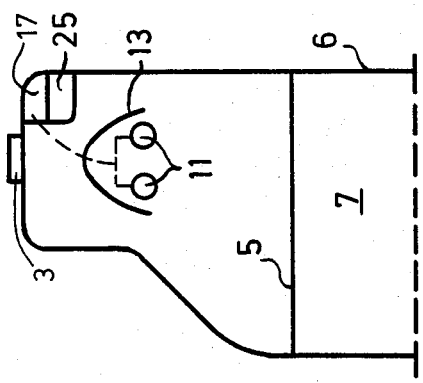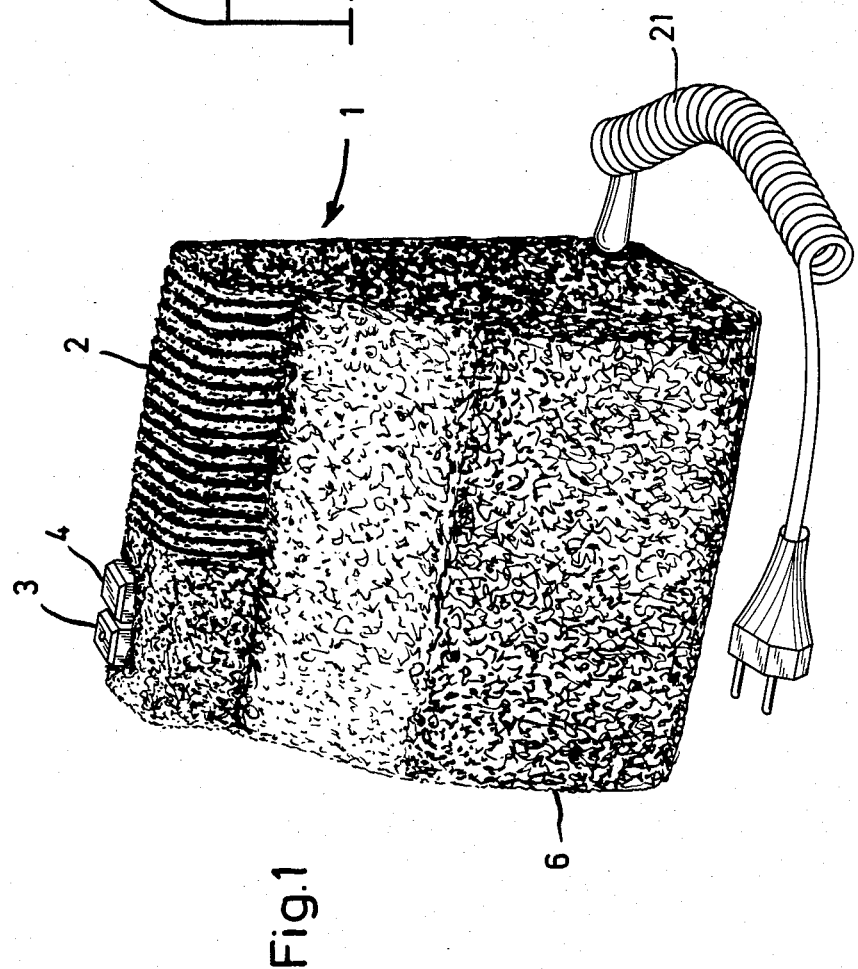

DEVICE FOR RAPID DEMONSTRATION OF THE ACTION OF PHOTOTROPIC OBJECTS

SUMMARY OF THE INVENTION

The present invention relates to a device for rapidly demonstrating the action of phototropic objects, particularly eyeglasses.

Phototropic eyeglasses automatically darken in bright daylight, the darkening being stimulated or excited by short-wave radiation. The brightening of the glasses takes place under the influence of heat and long-wave radiation.

If the action of phototropic glasses is to be demonstrated, for instance when the optician is advising a customer, then a source of light which emits short-wave radiation of sufficient intensity is necessary.

Demonstration instruments which contain such a source of light are known. Such an instrument is sold under the name UMBRATEST by the Carl Zeiss firm of Oberkochen, West Germany. This apparatus contains a mercury-vapor high-pressure lamp to the light of which the glasses to be demonstrated are exposed. A reduction in the light transmittance of the glass is obtained within a period of irradiation of about one minute. Aside from the fact that the full reduction of the light transmission is not obtained, the radiation time is frequently felt to be excessively long and the instrument is not ready for use immediately when required since the lamp must first warm up for a few minutes.

A demonstration instrument is also known into which the objects to be demonstrated are inserted and then, after closing the instrument, exposed therein to an electron flash of very high intensity. This instrument has the serious drawback that the phototropic effects cannot build up in normal manner. This shows itself, inter alia, in the color of the darkened glass, which differs from the color of normally acting glasses.

The object of the present invention is to provide a device which makes it possible rapidly to demonstrate the effect of phototropic objects without causing any impairment to the phototropic properties.

This object is achieved in accordance with the invention by a device which has at least one electron flash tube provided with a reflector, and a recess to receive the object being demonstrated, and a circuit to cause automatically a plurality of flashes at a predetermined time interval.

By the use of a plurality of successive flashes the amount of light necessary to demonstrate the darkening is applied in individual doses so that the phototropic effects can build up normally and the glass retains its normal color, for example gray.

It has proven advisable to develop the apparatus in such a manner that upon a single actuation five flashes, for instance, are given off within 10 seconds.

A flash tube is used which, in addition to emitting visible light, also emits ultraviolet light (UV-A), as can be obtained, for instance, by the use of a hard-glass bulb without filter coating. The protective pane arranged in the housing between flash tube and housing recess also absorbs practically no UV-A so that sufficient short-wave light is available on the object being demonstrated. UV-A radiation, by definition, lies within a wavelength range of 315 to 380 nm. The wavelength range of visible light (380–780 nm) is directly adjacent said range.

In addition to the fact that the instrument is practically immediately ready for use, darkening of the object being demonstrated is obtained in a very short period of time without having to tolerate any disturbing effects.

The recess in the housing advantageously has a rectangular base area of such size as to receive an eyeglass frame with the lenses contained in it. In order to assure uniform illumination of the hollow space which is thus formed it is advisable to use two adjacent straight flash tubes with which a common parabolic reflector is associated.

Since dazzling of the operator and of the customer is to be avoided in all cases, a switch is provided in the housing, which switch makes it possible to give off the flashes in the position of use but prevents this when the housing is tilted more than a predetermined small amount. In its position of use the housing is vertical and its recess is placed over the object to be demonstrated, such as eyeglasses in their regular frames, which lie on a suitable horizontal support such as a table or desk.

BRIEF DESCRIPTION OF THE DRAWINGS

The invention will be explained in further detail below with reference to the accompanying drawings, in which:

FIG. 1 shows one illustrative embodiment, seen in perspective;

FIG. 3 is a schematic cross section through the device.

DETAILED DESCRIPTION

Figure 2:
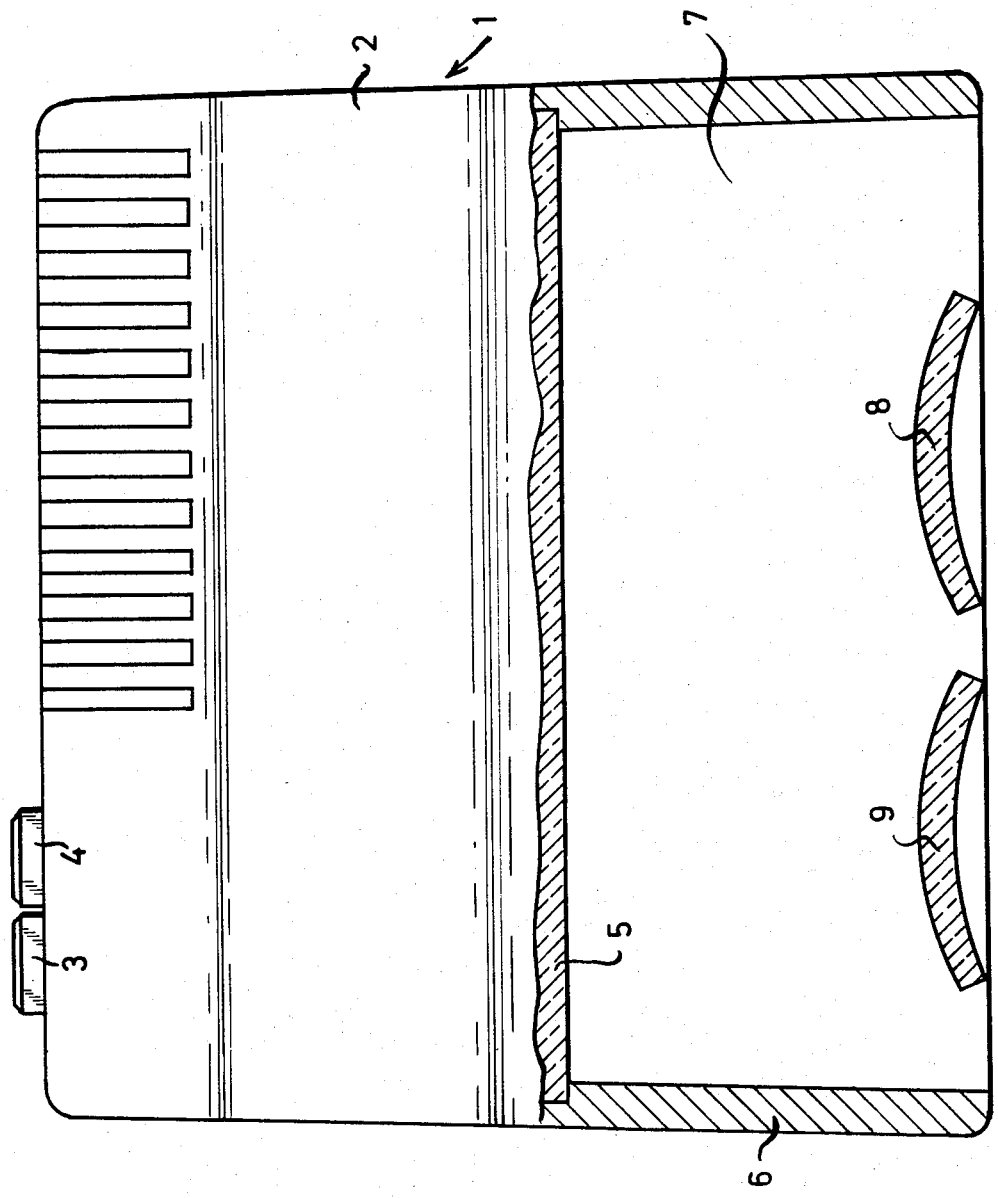
FIG. 2 is a front elevational view, with parts broken away and parts in section.

Referring to the drawings, the demonstration instrument is shown in general at 1. In its upper housing part 2 there are arranged, parallel to each other and side by side, two straight flash tubes 11 with associated parabolic reflector 13, as well as the circuit (schematically indicated at 17) which serves for operating these flash tubes and which is powered from a conventional plug-in cord 21. A button switch 3, when depressed, activates the circuit to give a sequence of flashes of, for instance, 5 flashes in 10 seconds. This sequence of flashes is produced by a single depression of the button 3 and is indicated optically by the pilot bulb 4. The rated work of a flash is about 70 Ws.

Below the flash tubes there is a protective pane 5 which is partially visible in FIG. 2. The flash tubes are developed in such a manner that UV-A radiation is emitted; the protective pane 5 is developed in such a manner that, for all practical purposes, it does not absorb this radiation. The lower housing part 6 is developed as a hollow space 7 which has a rectangular base area of such size that an eyeglass frame with lenses inserted therein has room in it.

In operation, the instrument is placed over the object to be demonstated, which rests on any available flat surface, as shown in FIG. 2. Here two eyeglass lenses 8 and 9 are used as the object. In the hollow space 7 within the housing part 6 there is also room for a large eyeglass frame or a binocular sample holder.

The circuit 17 of the instrument is developed in such a manner that, in the position of use shown in the drawings, when the device rests on a horizontal surface, a sequence of flashes can be produced by depressing the button 3, but that actuation of the flash is prevented when the device is tilted more than a predetermined small amount. This may be done by including in the circuit a conventional tilt-sensitive switch (of mercury type, for example) schematically shown at 25. This prevents production of flashes if one edge of the device is up at an elevation from the table, when a flash might be unpleasant to persons in the vicinity.

The instrument 1 is ready for use practically immediately; and does not require a preliminary warm-up interval. Upon depressing the button 3, a sequence of flashes is produced, the hollow space 7 being uniformly illuminated by light of short wavelength. After this sequence of flashes, the object being demonstrated has generally reached its full darkening. Of course, a second or third sequence of flashes can also be given if desired.

The kinetics and color of phototropic eyeglass lenses can be demonstrated rapidly and simply by the instrument described and shown. It is also possible, prior to the mounting of the glasses into the frame, to check whether the two lenses fit each other in color and transmittance and what difference are to be expected in the event of anisometropia and higher dioptric powers.

What is claimed is:

1. A device for rapidly demonstrating the action of phototropic objects such as eyeglasses, comprising a housing adapted to be placed on a support and provided with a recess (7) to receive an object being demonstrated (8, 9) while said object lies on said support, at least one electron flash tube and an associated reflector for directing a flash from said tube toward said object, said flash tube emitting UV-A radiation to impinge on said object, and circuit means which upon each actuation automatically produces a plurality of flashes which succeed each other at a predetermined time interval.

2. The invention defined in claim 1, wherein said circuit means includes switch means which makes it possible to actuate the flash tube in the position of use of the device but prevents actuation while the device is tilted more than a predetermined amount.

3. The invention defined in claim 1, wherein there are two straight flash tubes lying alongside of each other, a common parabolic reflector being associated with them.

4. The invention defined in claim 1, further comprising a protective pane (5) which does not absorb UV-A arranged between the flash tubes and the housing recess which receives said object.

5. The invention defined in claim 1, wherein said recess (7) of the housing has a rectangular base shape and is of such size that an eyeglass frame may be received in it.

6. The invention defined in claim 5, wherein said recess (7) is surrounded by an opaque housing wall (6).

* * * * *